US010575520B2

(12) United States Patent
Laine et al.

(10) Patent No.: US 10,575,520 B2
(45) Date of Patent: Mar. 3, 2020

(54) CYCLOHEXYLAMINE-BASED COMPOUNDS AND USES THEREOF

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventors: Roger A. Laine, Baton Rouge, LA (US); Lucas Veillon, Baton Rouge, LA (US); Gregg Henderson, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 62 days.

(21) Appl. No.: 15/459,656

(22) Filed: Mar. 15, 2017

(65) Prior Publication Data
US 2017/0265464 A1    Sep. 21, 2017

Related U.S. Application Data

(60) Provisional application No. 62/309,143, filed on Mar. 16, 2016.

(51) Int. Cl.
*A01N 33/04* (2006.01)
*A01N 25/08* (2006.01)

(52) U.S. Cl.
CPC ............ *A01N 33/04* (2013.01); *A01N 25/08* (2013.01)

(58) Field of Classification Search
None
See application file for complete search history.

(56) References Cited

U.S. PATENT DOCUMENTS

| | | | |
|---|---|---|---|
| 2,363,561 A * | 11/1944 | Smith | A61K 31/135 422/38 |
| 2,387,538 A | 10/1945 | Cantrell et al. | |
| 2,403,763 A | 7/1946 | Cantrell et al. | |
| 2,519,388 A * | 8/1950 | Loukomsky | D06M 11/44 427/381 |
| 2,588,318 A * | 3/1952 | Benignus | A01N 25/02 514/737 |
| 3,154,438 A | 10/1964 | Friedrich et al. | |
| 3,462,445 A * | 8/1969 | Muller | C07D 211/70 514/919 |
| 4,143,153 A | 3/1979 | Pommer et al. | |
| 5,061,698 A | 10/1991 | Malouf et al. | |
| 5,276,029 A | 1/1994 | Goettsche et al. | |
| 5,778,596 A * | 7/1998 | Henderson | A01M 1/2011 43/124 |
| 2005/0042246 A1* | 2/2005 | Rojas | A01N 25/006 424/410 |

FOREIGN PATENT DOCUMENTS

| | | |
|---|---|---|
| WO | WO-8505380 | * 12/1985 |
| WO | WO1997021349 A1 | * 6/1997 |
| WO | WO-0036914 | * 11/1999 ............. A01N 31/16 |

OTHER PUBLICATIONS

Rios-Mercadillo et al. (JACS 101:19 5828-5829) (Year: 1979).*
"?-L-Fucose 1-phosphate bis-(cyclohexylamine) salt (CAS 24333-03-7)", Market Research Report 2017, [Online]. Retrieved from the Internet: <URL: https://marketpublishers.com/r/L404081CBD7EN.html>, (Accessed Jun. 15, 2017), 5 pgs.
"International Application Serial No. PCT/US2017/022528, International Search Report dated Aug. 1, 2017", 4 pgs.
"International Application Serial No. PCT/US2017/022528, Written Opinion dated Aug. 1, 2017", 7 pgs.

* cited by examiner

*Primary Examiner* — Celeste A Roney
(74) *Attorney, Agent, or Firm* — Thomas | Horstemeyer, LLP

(57) ABSTRACT

Compositions are described comprising an amount of a toxicant comprising a compound of the formula $HNR^1R^2$, or a salt thereof, wherein $R^1$ and $R^2$ are independently hydrogen, a substituted or unsubstituted $C_4$-$C_6$-cycloalkyl group or a substituted or unsubstituted $C_6$-$C_{12}$-aryl group; wherein the amount of the toxicant is sufficient to control termites. Methods for controlling termites using such compositions are also described.

20 Claims, No Drawings

CYCLOHEXYLAMINE-BASED COMPOUNDS AND USES THEREOF

CROSS-REFERENCE TO RELATED APPLICATIONS

This application claims the benefit of priority from U.S. Provisional Appl. Ser. No. 62/309,143, filed Mar. 16, 2016, the entirety of which is incorporated by reference as if fully set forth herein.

BACKGROUND

The Formosan subterranean termite, *Coptotermes formosanus* Shiraki, is a major worldwide pest that attacks both living trees and structural wood. Unlike other subterranean termites, the Formosan termite can establish a colony that does not touch the ground.

*Coptotermes formosanus* is native to southeast Asia, but is now also found in Hawaii, along the southeastern Atlantic coast of the United States, and in the Gulf South of the United States. First discovered in the United States in 1965, *C. formosanus* has gradually expanded its geographic domain. The largest single locus of *C. formosanus* in the United States is in south Louisiana, with heavy infestations in Lake Charles and New Orleans. *C. formosanus* may in some cases displace native *Reticulitermes* spp.

There is a continuing need for improved techniques for causing mortality to termites because of the ongoing infestation threats.

DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The various embodiments described herein relate to a composition comprising: an amount of a toxicant comprising a compound of the formula $HNR^1R^2$, or a salt thereof, wherein $R^1$ and $R^2$ are independently hydrogen, a substituted or unsubstituted $C_4$-$C_6$-cycloalkyl group or a substituted or unsubstituted $C_6$-$C_{12}$-aryl group; wherein the amount of the toxicant is sufficient to control termites (e.g., Formosan subterranean termites).

As used herein, the term "control termites" refers to at least causing a percent mortality of a termite population of about 50% to about 100% within a period of from about 5 days to about 14 days.

In some embodiments, at least one of $R^1$ and $R^2$ is a substituted or unsubstituted $C_4$-$C_6$-cycloalkyl group. In other embodiments, $R^1$ and $R^2$ are each a substituted or unsubstituted $C_4$-$C_6$-cycloalkyl group. The substituted or unsubstituted $C_4$-$C_6$-cycloalkyl group can be a substituted or unsubstituted cyclohexyl group.

Salts of the compound of the formula $HNR^1R^2$ are contemplated herein. Salts of the compound of the formula $HNR^1R^2$ are salts of the formula:

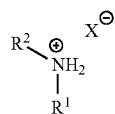

wherein $R^1$ and $R^2$ are as defined herein and $X^-$ is a counterion. The counterion can be any suitable counterion including halide (e.g., chloride, bromide, and iodide), phosphate (e.g., glycerol-3-phosphate), sulfate, and carboxylate (e.g., acetate, benzoate, and citrate).

The term "cycloalkyl," as used herein, refers to substituted or unsubstituted cycloalkyl groups having from 3 to 20 carbon atoms (e.g., $C_3$-$C_{20}$, $C_3$-$C_{10}$, $C_3$-$C_6$, and $C_3$-$C_6$). Examples of cycloalkyl groups include cyclopropyl, cyclobutyl, cyclopentyl, and cyclohexyl groups.

The term "aryl," as used herein, refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 18 carbons ($C_6$-$C_{18}$; e.g., $C_6$-$C_{12}$; $C_6$-$C_{10}$; and $C_{12}$-$C_{18}$) in the ring portions of the groups. Representative substituted aryl groups can be mono-substituted or substituted more than once, such as, but not limited to, 2-, 3-, 4-, 5-, or 6-substituted phenyl or 2-8 substituted naphthyl groups.

The cycloalkyl, aryl, etc., groups described herein can be substituted or unsubstituted. The term "substituted" as used herein refers to a group (e.g., cycloalkyl and aryl) or molecule in which one or more hydrogen atoms contained thereon are replaced by one or more "substituents." The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, acyl, cycloalkyl, aryl, aralkyl, heterocyclyl, heteroaryl, or heteroarylalkyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aralkyl," "arylalkyl," and "aryl-alkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "heteroaralkyl" and "heteroarylalkyl" as used herein refers to alkyl groups as defined herein in which a hydrogen or carbon bond of an alkyl group is replaced with a bond to a heteroaryl group as defined herein.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_6$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The compositions of the various embodiments described herein can further comprise at least one termite attractant. As used herein, the term "attractant" refers to a compound or compounds that, among other things, stimulates the termites to locate compositions comprising compounds of the formula $HNR^1R^2$ or salts thereof over other compositions and/or their regular food source. The attractant may also stimulate termites to feed on compositions containing the attractant over other compositions and/or their regular food source. Non-limiting examples of attractants include 3β-hydroxyandrost-5-en-17-one; 4β-ethylstigmasta-7,24(28)-dien-3-one; stigmast-4-en-3-one; cholest-5-en-3β-ol; androst-4-ene-3,17-dione; androst-4-ene-3β-diol; stigmasta-4,22-dien-3-one; and androst-5-en-3β-ol.

The compositions of the various embodiments described herein can further comprise at least one termite feeding stimulant. The feeding stimulate stimulates termites to feed on compositions containing the stimulant over other compositions and/or their regular food source. Non-limiting examples of feeding stimulant include 2,6-di-t-butyl-4-methyl-phenol, naphthalene, hexanedioic acid dioctyl ester, and dioctyl phthalate.

The compositions of the various embodiments described herein can further comprise at least one bait material. Non-limiting bait materials include at least one of cardboard, paper, sugarcane, corn cobs, and dried semi-aqueous cellulose mixtures.

The compositions of the various embodiments described herein can further comprise a solvent (e.g., organic solvents, such as alkanols, such as ethanol; aromatics, such as xylenes; ketones, such as acetone; plant-derived oils, such as those derived from corn cobs; and petroleum fractions). In some embodiments, the solvent is substantially aqueous. As used herein, the term "substantially" and "substantial" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The compositions of the various embodiments described herein can further comprise a pesticide. Combinations of a toxicant of the various embodiments described herein in an amount of sufficient to control termites and an effective amount of one or more pesticides are also contemplated herein. The one or more pesticides is not limited. Examples of pesticides include 1,2-dichloropropane, 1,3-dichloropropene, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bioresmethrin, bistrifluoron, borax, boric acid, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, cinerin I, cinerin cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosaur, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprpx, fluvalinate, fonofos, formetanate, formothion, formparanate, fosmethilan, fospirate, fosthietan, furathiocarb, furethrin, gamma-cyhalothrin, gamma-HCH, halfenprox, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin H, jodfenphos, juvenile hormone I, juvenile hormone II, juvenile hormone Ill, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methyl bromide, methylchloroform, methylene chloride, metofluthrin, metolcarb, metoxadiazone, mevinphos, mexacarbate, milbemectin, milbemycin oxime, mipafox, mirex, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxydemetonmethyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DOT, prallethrin, precocene I, precocene II, precocene Ill, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulfoxaflor, sulfluramid, sulfotep, sulfuryl fluoride, sulprofos, tau-fluvalinate, tazimcarb, TOE, tebufenpyrad, tebupirimfos, teflubenzuron, tefluthrin, temephos, TEPP, terallethrin, terbufos, tetrachloroethane, tetrachlorvinphos, tetramethrin, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, and zolaprofos.

As used herein, the term "amount of the toxicant that is sufficient to control termites" refers to an LD30 (Lethal Dose Killing 30% of the termites in a specified time, such as 14 days) and an LD70. In some embodiments, the LD30 can be the equivalent concentration of 0.30 µg/300 µL solvent added to a 42 mm×3 µm filter paper circle, for example, to about 0.60 µg/300 µL. In some embodiments, the LD70 can be from about 0.60 µg/300 µL to about 1 µg/300 µL.

The various embodiments described herein also relate to a method for controlling termites, the method comprising contacting termites with the various composition described herein. As used herein, the term "contact" and "contacting" comprise situations when any external or internal surface of a termite comes in contact with the compositions of the various embodiments described herein. The term "contact" and "contacting" therefore comprises contact with any external surface on a termite, hence "topical contact," including contact with one or more of a termite's head or any part thereof (e.g., antennae and eyes); thorax or any part thereof; abdomen or any part thereof; and legs. But the term also encompasses instances where termites ingest the compositions of the various embodiments described herein, whether by eating or imbibing the compositions. As described herein, the term "control termites" refers to at least causing a percent mortality of a termite population of about 50% to about 100% within a period of from about 5 days to about 14 days.

Various embodiments relate to a substrate comprising the compositions of the various embodiments described herein. Non-limiting substrates include any cellulosic material including wood and paper (e.g., cardboard). In some embodiments, the substrate can be impregnated with the compositions of the various embodiments described herein.

In some embodiments, the substrate can be an indoor or outdoor surface. Some embodiments therefore relate to an indoor or outdoor surface wherein the surface comprises a composition of the various embodiments described herein and the composition causes mortality in termites. As used herein, the term "surface" includes any surface, whether located indoor or outdoor. The surface is, in some embodiments, at least one of an interior and an exterior portion (e.g., a wall or crawlspace) of a building. In other embodiments, the surface also includes a surface that is inside or outside of a trap, such as an insect trap (e.g., a bait trap).

The compositions of the various embodiments described herein can comprise various inert and active ingredients known in the art. Examples of the various ingredients contained in the compositions described herein include carriers (e.g., organic solvents, such as alkanols, such as ethanol; aromatics, such as xylenes; ketones, such as acetone; plant-derived oils, such as those derived from corn cobs; and petroleum fractions), emulsifiers, stabilizers, and uptake enhancers.

The species of termites to which the methods of the various embodiments described herein are not limited. Examples of species of termites to which the methods of the various embodiments described herein apply include *C. formosanus* and *Reticulitermes* spp.

Other embodiments relate to methods of causing the substantial deterioration of termite antennae comprising contacting termites with the compositions of the various embodiments described herein. As used herein, the term "deterioration" refers to a substantial shortening, whether ablative or segmented distal shortening, of at least one of the antennae of a termite.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

Examples

The following examples are included to demonstrate specific embodiments of the invention. However, many changes can be made in the specific embodiments which are disclosed and still obtain a like or similar result without departing from the spirit and scope of the invention.
Materials and Methods
Insect Collection and Maintenance Worker *C. formosanus* were collected from Brechtel Park, New Orleans, La. by methods known in the art. Bait crates (open-mesh plastic containers) filled with southern yellow pine or spruce-pine-fir sapwood were arranged into a lattice and buried near a *C. formosanus* infested tree and collected after 3 to 9 weeks. Termite-containing crates were held in 250-liter plastic garbage cans kept at room temperature (26-28 C) and 70-80% relative humidity with the original food source. Termites were collected from New Orleans on 13 Jun. 2006 (collection group A); 9 Aug. 2006 (collection group B); 1 Mar. 2008 (collection group C); 9 May 2008 (collection group D); 20 May 2008 (collection group E); 20 Mar. 2009 (collection group F); 29 May 2009 (collection group G) and 11 May 2010 (collection group H); 18 Aug. 2012 (collection group I); May 2014 (collection group J); August 2014 (collection group K). The termite collection procedure was tapping infested wood sticks into clean plastic containers where termites were collected on moistened paper towels.
Chemicals Neutral red dye, 2-phospho-myo-inositol (di-cyclohexylamine salt), glycerol-3-phosphate (dicyclohexylamine salt) and cyclohexylamine were obtained from Sigma-Aldrich (St. Louis, Mo.). D-galactose and D-glucose were obtained from Matheson Coleman and Bell (Cincinnati, Ohio) and Fisher Scientific (Fair Lawn, N.J.) respectively. Dicyclohexylamine phosphate was synthesized by titrating 85% phosphoric acid into a 1M solution of cyclohexylamine in a 2:1 molar ratio of neat cyclohexylamine:85% phosphoric acid solution. After being allowed to react for 24 hours, the resulting solution was stored in a glass beaker for approximately one week at room temperature until large crystals formed. The pinkish crystalline product was gently scraped from the beaker and collected for use. Monocyclohexylamine phosphate was synthesized by carefully titrating 85% phosphoric acid into neat cyclohexylamine in a 1:1 molar ratio. Analysis using X-ray crystallography elucidated and confirmed the identity of the product crystals for both mono- and dicylohexylamine phosphate that were subsequently used for testing.
Dose-Response Feeding Assays 2-phospho-myo-inositol (dicyclohexylamine salt), glycerol-3-phosphate (dicyclohexylamine salt), dicyclohexylamine phosphate, monocyclohexylamine phosphate, and neat cyclohexylamine were screened for termiticide activity as follows: test compounds were applied to 42.5 mm×3 μm filter papers, in 60×15 mm plastic Petri dishes, in a solution of 1 mg of test compound per 10 μL of distilled water. Doses of 2.5 mg (160.2 μg/mm$^3$ of filter paper), 5 mg (320.4 μg/mm$^3$) 10 mg (640.8 μg/mm$^3$), and 20 mg (1281.7 μg/mm$^3$) of 2-phospho-myo-inositol were examined. Following filter paper treatment distilled water was added to bring the total volume applied to the filter papers to 300 μL, using 300 μL of distilled water as control. Cyclohexylamine was applied to the paper diluted in amounts of 300 μL, in concentrations ranging from 0.626 to 10.2 μg/mm$^3$. To prevent desiccation, approximately 50 μL of distilled water was applied to filter paper throughout the trials every third day, or upon observing that a filter paper disc was relatively dry. To test whether termite mortality was induced by consumption of the cyclohexylamine-treated paper, or whether vapor presence of cyclohexylamine was responsible for the toxicity, we compared addition of cyclohexylamine to both paper and fiberglass filters—the latter of which they will not consume. In addition to pure cyclohexylamine, dicyclohexylamine phosphate and monocyclohexylamine phosphate were tested for toxicity. Dicyclohexylamine phosphate was tested in concentrations ranging from 0.348 to 348 μg/mm$^3$, and monocyclohexylamine phosphate was tested in concentrations ranging from 2.28 to 228 μg/mm$^3$. Replicates of twenty worker termites were incubated in the dark in a parafilm-sealed Petri dish at room temperature for 2 weeks. Termite mortality was recorded daily in triplicate experiments. An analysis of variance (ANOVA) (SAS ANOVA procedure) followed by Tukey's Studentized range test was used to evaluate statistical differences among groups (Institute 1989). All mortality data were judged at a=0.05.

Termites from collection group B were used in the 2-Phospho-Myo-Inositol dose mortality assay. Termites from collection groups C and D were used in both the dicyclohexylamine-2-phophoinositol, and dicylclohexyalmine-glycerol-3-phosphate dose mortality assay. Termites from collection group I were used in cyclohexylamine dose mortality assays. Termites from collection group were used in the dicyclohexylamine phosphate and neat cyclohexylamine volatility dose mortality assays. Termites from collection group K were used in the monocyclohexylamine phosphate dose mortality assay.

In dose mortality experiments where paper consumption data are shown, filter papers were weighed in ambient humidity prior to sugar application. After 14 days termites were removed from the dishes and the filter paper from each replicate was cleaned, washed of residual carbohydrate and dried at 100 C for 24 h. After drying and humidity equilibration for 24 h, filter papers were reweighed for determination of paper consumption. An analysis of variance (ANOVA) (SAS ANOVA procedure) followed by Tukey's Studentized range test was used to evaluate statistical differences among groups (Institute 1989). All consumption data were judged at a=0.05.

Termite Antenna Ablative Shortening Induced by 2-Phospho-Myo-Inositol as the Dicyclohexylamine Salt Fifty worker termites, from collection group B, were placed in a 60×15 mm polystyrene petri dish with 42.5 mm filter paper treated with 10 mg of 2-phospho-myo-inositol (640.8 µg/mm$^3$). Daily for 14 day three randomly selected termites were removed, euthanized with 5 µL of ethanol and their antennae were photographed, after which, GSA image analyzer was used to quantify the length of the termite antennae (Bansemer and Scheel 2010). Antenna length data were subjected to ANOVA followed by Tukey's Studentized range test (Institute 1989). All data were judged at α=0.05. All experiments were performed in triplicate.

Protozoan Counting

The effect of 2-phospho-myo-inositol dicyclohexylamine salt on *C. formosanus* hindgut protozoan populations was examined as follows: Ten mg of 2-phospho-myo-inositol were dissolved in 200 µL of distilled water and applied to filter paper, in a 60×15 mm plastic Petri dish, (640.8 µg/mm$^3$). Control filter paper received 200 µL of distilled water. With 75 worker termites per dish, collection group A were used. *Pseudotrichonyrnpha grassii* Koidzumi, *Holornastigotoides hartmanni* Koidzumi and *Spirotrichonympha leidyi* Koidzumi were counted daily for 2 week as described in Mannesmann, R., Z. Angew. Entomol. 72: 116-128 (1972); and modified by Maiastrello, L., et al., Pest Manag. Sci. 59: 58-68 (2002). Hindguts were removed from the posterior ends of three workers and gently macerated in 40 µL saline solution containing neutral red dye (0.5 mL of 1% aqueous neutral red solution dissolved in 10 mL saline solution). The number of each protozoan species was determined using a hemocytometer (Bright-line Improved Neubauer, Hausser Scientific, Horsham, Pa.) under a light microscope. The population of each protozoan species per hindgut ($X_F$) was calculated as: $X_F=(G \times n)/(V \times 3)$, where G=volume (µL) of solution hindguts dissected in; n=mean of two counts within hemocytometer; V=volume (µL) of area counted. Mean (±SE) $X_F$ values calculated from two replicates were used for graphical comparison of data. Protozoan population data were subjected to ANOVA followed by a Tukey's Studentized range test (SAS Institute 1989), all data were judged at α=0.05. A square root transformation was applied for data analysis, however untransformed means are reported.

Results

2-Phospho-Myo-Inositol (1281.7, 640.8, 320.4 and 160.2 µg/mm$^3$): Concentration-Dependent Toxicity.

In this assay the three lowest concentrations applied, 640.8, 320.4 and 160.2 µg/mm$^3$, did not result in mortality significantly different from the control group. Mortality observed in the highest dosage group, 1281.7 µg/mm$^3$, became significant on day eight and thereafter. Forty three percent mortality was observed on day eight, after which it increased linearly to 98% on day 14.

Quantifying Termite Antennae Length. 2-Phospho-Myo-Inositol (640.8 µg/mm$^3$): Segmented Distal Shortening.

A 640.8 µg/mm$^3$ myo-inositol-2-monophosphate treatment resulted in significantly reduced termite antennae of day five and six and eight through 14.

Protozoa Quantification. 2-Phospho-Myo-Inositol Bioassay (640.8 µg/mm$^3$): Reduced Populations.

A 640.8 µg/mm$^3$ treatment of ins2P resulted in reduced total protozoan populations day four and thereafter during the 14 day assay *H. hartmanni* populations were significantly reduced on day one, two, five, eight, nine, 10, 11 and 14. *P. grassii* populations were also significantly lowered on day one, five, eight, nine, 10 and 11. *S. leidyi* populations were affected the least, only being significantly lower than controls on day nine and 11.

Dose-Response Feeding Assays.

Glycerol-3-Phosphate Dicyclohexylamine Salt (320.4, 640.8 µg/mm$^3$)

Both concentrations tested resulted in mortality significantly different from the control. In the higher dosage group, mortality became significant on day 5 and increased in a linear fashion, reaching 98% mortality on day 12. In the lower dosage group, mortality became significant on day 12 and increased to 71% on day 14.

Neat Cyclohexylamine (3.39, 5.08, 10.2 µg/mm$^3$)

All dosage groups displayed 100% mortality within one to three days. 100% mortality was observed on day one of the highest dosage, 10.2 µg/mm$^3$, and on day three of the lowest dosage, 3.39 µg/mm$^3$.

Neat Cyclohexylamine (1.0, 1.7, 2.4 µg/mm$^3$)

Only the two highest dosage groups displayed mortality significantly different from the control. Mortality for the highest dosage, 2.4 µg/mm$^3$, became significant on day five and increased to 41% on day 14. Mortality for 1.7 µg/mm$^3$ became significant on day eight and increased to 33% on day 14.

Neat Cyclohexylamine (0.62, 0.82, 1.25, 2.51 µg/mm$^3$)

In this assay, only the highest dosage group, 2.51 µg/mm$^3$, displayed significantly different mortality. In this group, mortality became significantly different on day six and thereafter. 16% mortality was observed on day six, after which it increased to 63% on day 14.

Dicyclohexylamine Phosphate (17.22, 34.44, 68.88 µg/mm$^3$)

All three concentrations groups were observed to be significantly different than the control group. The highest final mortality value was observed in the highest dosage group, 68.88 µg/mm$^3$. In this group, mortality became significantly different on day five and increased in linear fashion until 45% mortality was reached on day 14.

Dicyclohexylamine Phosphate (1.22, 2.45, 4.90, 9.80 µg/mm$^3$)

FIG. 21: The two highest dosage groups, 4.90 and 9.80 µg/mm$^3$, displayed mortality significantly different than the control. In dosage group 4.90 µg/mm³, mortality became significantly different on day three and increased to 38% on day 14. In dosage group 9.8 µg/mm³, mortality became significantly different on day four and increased to 36% on day 14.

Dicyclohexylamine Phosphate (0.348, 348 µg/mm³)

In this assay, mortality in both concentrations was observed to be significantly higher than the control. Treatment with the higher dosage, 348 µg/mm³, resulted in 100% mortality upon the first day. The mortality of the lower dosage group, 0.348 µg/mm³, was observed to become significantly higher on day three and continued to increase until reaching 28% on day 14.

Monocyclohexylamine Phosphate (2.28, 22.8, 228 µg/mm³)

In this assay only mortality in the highest dosage group, 228 µg/mm³, was observed to be significantly different from the control. Mortality became significantly different on day 10, reaching a value of 38%, and eventually increased to 100% on day 14. Mortality for the two lower dosage groups was not significantly different from the control.

Cellulose Consumption.

Neat Cyclohexylamine (0.626, 0.822, 1.253, 2.510 µg/mm³): Reduced Cellulose Consumption.

In this assay, the three highest dosage groups, 0.822, 1.253 and 2.510 µg/mm³, resulted in consumption rates (per surviving termites) that were significantly lower than the control group (FIG. 15). The lowest dosage applied, 0.626 µg/mm³, did not result in a consumption rate per termite significantly different from the control group (FIG. 15), Cyclohexylamine Volatile Effects.

Neat Cyclohexylamine (600 µg): Consumption-Dependent Toxicity.

In this assay, neat cyclohexylamine treatment of cellulose resulted in significantly different mortality than the corresponding control group, becoming significantly different on day eight and thereafter. 25% mortality was observed on day eight, increasing until reaching 45% on day 14. Cyclohexylamine treatment of fiberglass did not result in mortality significantly different than that of the corresponding control group. Mortality for the fiberglass control and cellulose control was not observed to be significantly different.

Discussion

Cyclohexylamine was found to be a potent toxicant to Formosan Subterranean Termites, as a neat compound, in sugar phosphate salt forms and in 2 different phosphate salt forms. The toxicity manifested in concentrations at the LD30-LD70 level as a most unusual specific sequential ablation of the termite antennae over a 3-14 day time frame. The reason for specific loss of antennae is not known, however, the effect on termite workers is to cease normal behaviors, which are stimulated and monitored by the chemosensorium of the termite cuticle. Termites become increasingly moribund as their antennae are incrementally degraded, finally ceasing feeding, and movement when the antennae are completely gone. Practically, the myo-inositol-2-phosphate and glycerol-3-phosphate salts of cyclohexylamine are too expensive to consider for termite toxicants, and neat cyclohexylamine is volatile, and noxious. Therefore we prepared the less expensive mono- and dicyclohexylamine phosphate salts made simply from phosphoric acid and cyclohexylamine, producing easily crystallizable compounds that can be added to paper baits to effect a slow-acting toxin at 14 day LD30-70 levels that have the potential of seriously disrupting a colony with trophallaxis feeding of the soldiers and queen.

The present invention provides for the following embodiments, the numbering of which is not to be construed as designating levels of importance:

Embodiment 1 relates to a composition comprising: an amount of a toxicant comprising a compound of the formula $HNR^1R^2$, or a salt thereof, wherein $R^1$ and $R^2$ are independently hydrogen, a substituted or unsubstituted $C_4$-$C_6$-cycloalkyl group or a substituted or unsubstituted $C_6$-$C_{12}$-aryl group; wherein the amount of the toxicant is sufficient to control termites.

Embodiment 2 relates to the composition of Embodiment 1, wherein at least one of $R^1$ and $R^2$ is a substituted or unsubstituted $C_4$-$C_6$-cycloalkyl group.

Embodiment 3 relates to the composition of Embodiment 1, wherein $R^1$ and $R^2$ are each a substituted or unsubstituted $C_4$-$C_6$-cycloalkyl group.

Embodiment 4 relates to the composition of Embodiment 1, wherein the substituted or unsubstituted $C_4$-$C_6$-cycloalkyl group is a substituted or unsubstituted cyclohexyl group.

Embodiment 5 relates to the composition of Embodiment 1, wherein the toxicant comprises a salt of the compound of the formula $HNR^1R^2$.

Embodiment 6 relates to the composition of Embodiments 1-5, wherein the salt of the compound of the formula $HNR^1R^2$ is a phosphate salt.

Embodiment 7 relates to the composition of Embodiment 1-6, wherein the phosphate salt is the glycerol-3-phosphate salt.

Embodiment 8 relates to the composition of Embodiments 1-7 further comprising at least one termite attractant.

Embodiment 9 relates to the composition of Embodiments 1-8 further comprising a termite feeding stimulant.

Embodiment 10 relates to the composition of Embodiments 1-9 further comprising at least one bait material.

Embodiment 11 relates to the composition of Embodiment 10, wherein the bait material comprises at least one of cardboard, paper, sugar cane, corn cobs, and dried semi-aqueous cellulose mixtures.

Embodiment 12 relates to the composition of Embodiments 1-11 further comprising a solvent.

Embodiment 13 relates to the composition of Embodiment 12, wherein the solvent is substantially aqueous.

Embodiment 14 relates to the composition of Embodiments 1-13 further comprising a pesticide.

Embodiment 15 relates to the composition of Embodiments 1-14, wherein the amount of the toxicant that is sufficient to control termites is between an LD30 and an LD70.

Embodiment 16 relates to a method for controlling termites, the method comprising contacting termites with the composition of Embodiments 1-15.

Embodiment 17 relates to the method of Embodiment 16, wherein the controlling comprises causing a percent mortality of a termite population of about 50% to about 100% within a period of from about 5 days to about 14 days.

Embodiment 18 relates to the method of Embodiments 16-17, wherein the termites comprise Formosan subterranean termites.

Embodiment 19 relates to a substrate comprising the composition of Embodiments 1-15.

Embodiment 20 relates to the substrate of Embodiment 19, wherein the substrate is cardboard or paper.

Embodiment 21 relates to a method of causing the substantial deterioration of termite antennae comprising contacting termites with the composition of Embodiments 1-15.

Embodiment 22 relates to an indoor or outdoor surface wherein: (a) the surface comprises a composition of Embodiments 1-15; and (b) the composition causes mortality in termites.

Embodiment 23 relates to the surface of Embodiment 22, wherein the surface is at least one of an interior or exterior wall of a building.

Embodiment 24 relates to the surface of Embodiment 22, wherein the surface is inside or outside of a trap.

What is claimed is:

1. A composition comprising:
    an amount of a toxicant comprising a glycerol-3-phosphate salt of the compound of the formula $HNR^1R^2$, wherein $R^1$ and $R^2$ are independently hydrogen, a substituted or unsubstituted $C_4$-$C_6$-cycloalkyl group or a substituted or unsubstituted $C_6$-$C_{12}$-aryl group;
    wherein the amount of the toxicant is sufficient to kill at least 30% of a population of termites in 14 days, and wherein the amount of the toxicant is between about 0.0001% and about 0.01%; and
    a solvent.

2. The composition of claim 1, wherein at least one of $R^1$ and $R^2$ is a substituted or unsubstituted $C_4$-$C_6$-cycloalkyl group.

3. The composition of claim 1, wherein $R^1$ and $R^2$ are each a substituted or unsubstituted $C_4$-$C_6$-cycloalkyl group.

4. The composition of claim 1, wherein the substituted or unsubstituted $C_4$-$C_6$-cycloalkyl group is a substituted or unsubstituted cyclohexyl group.

5. The composition of claim 1 further comprising at least one termite attractant.

6. The composition of claim 1 further comprising a termite feeding stimulant.

7. The composition of claim 1 further comprising at least one bait material.

8. The composition of claim 7, wherein the bait material comprises at least one of cardboard, paper, sugar cane, corn cobs, and dried semi-aqueous cellulose mixtures.

9. The composition of claim 1, wherein the solvent is substantially aqueous.

10. The composition of claim 1 further comprising a pesticide.

11. The composition of claim 1, wherein the amount of the toxicant that is sufficient to control termites is between an LD30 and an LD70.

12. A method for controlling termites, the method comprising contacting termites with a composition comprising:
    an amount of a toxicant comprising a glycerol-3-phosphate salt of the compound of the formula $HNR^1R^2$, wherein $R^1$ and $R^2$ are independently hydrogen, a substituted or unsubstituted $C_4$-$C_6$-cycloalkyl group or a substituted or unsubstituted $C_6$-$C_{12}$-aryl group;
    wherein the amount of the toxicant is sufficient to kill at least 30% of a population of termites in 14 days, and wherein the amount of the toxicant is between about 0.0001% and about 0.01%; and
    a solvent.

13. The method of claim 12, wherein the controlling comprises causing a percent mortality of a termite population of about 50% to about 100% within a period of from about 5 days to about 14 days.

14. The method of claim 12, wherein the termites comprise Formosan subterranean termites.

15. A substrate comprising a composition comprising:
    an amount of a toxicant comprising a glycerol-3-phosphate salt of the compound of the formula $HNR^1R^2$, wherein $R^1$ and $R^2$ are independently hydrogen, a substituted or unsubstituted $C_4$-$C_6$-cycloalkyl group or a substituted or unsubstituted $C_6$-$C_{12}$-aryl group;
    wherein the amount of the toxicant is sufficient to kill at least 30% of a population of termites in 14 days, and wherein the amount of the toxicant is between about 0.0001% and about 0.01%; and
    a solvent.

16. The substrate of claim 15, wherein the substrate is cardboard or paper.

17. A method of causing the substantial deterioration of termite antennae comprising contacting termites with a composition comprising:
    an amount of a toxicant comprising a glycerol-3-phosphate salt of the compound of the formula $HNR^1R^2$, wherein $R^1$ and $R^2$ are independently hydrogen, a substituted or unsubstituted $C_4$-$C_6$-cycloalkyl group or a substituted or unsubstituted $C_6$-$C_{12}$-aryl group;
    wherein the amount of the toxicant is sufficient to kill at least 30% of a population of termites in 14 days, and wherein the amount of the toxicant is between about 0.0001% and about 0.01%; and
    a solvent.

18. An indoor or outdoor surface wherein:
    (a) the surface comprises a composition comprising:
    an amount of a toxicant comprising a glycerol-3-phosphate salt of the compound of the formula $HNR^1R^2$, wherein $R^1$ and $R^2$ are independently hydrogen, a substituted or unsubstituted $C_4$-$C_6$-cycloalkyl group or a substituted or unsubstituted $C_6$-$C_{12}$-aryl group;
    wherein the amount of the toxicant is sufficient to kill at least 30% of a population of termites in 14 days, and wherein the amount of the toxicant is between about 0.0001% and about 0.01%; and
    a solvent; and
    (b) the composition causes mortality in termites.

19. The surface of claim 18, wherein the surface is at least one of an interior or exterior wall of a building.

20. The surface of claim 18, wherein the surface is inside or outside of a trap.

* * * * *